United States Patent [19] [11] 4,112,100
Callahan et al. [45] Sep. 5, 1978

[54] METHODS OF USE OF PYRIDYLALKYL PHENYLTHIOUREAS

[75] Inventors: William A. Callahan, Richland Township, Kalamazoo County; Eldridge Myles Glenn, Kalamazoo; Douglas L. Rector, Parchment, all of Mich.

[73] Assignee: The Upjohn Company, Kalamazoo, Mich.

[21] Appl. No.: 590,273

[22] Filed: Jun. 25, 1975

Related U.S. Application Data

[63] Continuation-in-part of Ser. No. 428,373, Dec. 26, 1973, abandoned.

[51] Int. Cl.$^2$ ............................................. A61K 31/44
[52] U.S. Cl. ............................ 424/263; 260/294.8 G; 260/294.8 H
[58] Field of Search .................. 260/294.8 H; 424/263

[56] References Cited

U.S. PATENT DOCUMENTS

| | | | |
|---|---|---|---|
| 2,801,911 | 8/1967 | Gilbert et al. | 71/99 |
| 3,236,624 | 2/1966 | Martin et al. | 71/99 |
| 3,547,935 | 12/1970 | Diehl et al. | 260/297 |
| 3,682,788 | 8/1972 | Kardos et al. | 260/294.8 H |
| 3,700,678 | 10/1972 | Mihailovski | 260/295 E |

OTHER PUBLICATIONS

Sheob et al., "Indian J. Chem.", vol. 5, (1967), p. 145.
Xuong et al., "Med. Exp.", vol. 10, (1964), pp. 272–276.
Adkins et al., "J. Am. Chem. Soc.", vol. 66, (1944), pp. 1293–1295.
Murashoval et al., "Zh. Anal. Khim", vol. 24, (1969), pp. 1205–1207.
Novikov, "Khim, Geterotsikl Soedin", (1), (1968), pp. 115–116.
Novikov, "Chem. Abstracts", vol. 70, (1969), No. 3776p, Subject Index, vol. 70, p. 3386s.
Novikov, et al., "Chem. Abstracts", vol. 70, (1969), No. 77726u, Subject Index, vol. 70, p. 3383s.

*Primary Examiner*—Natalie Trousof
*Assistant Examiner*—R. W. Ramsuer
*Attorney, Agent, or Firm*—Martin B. Barancik

[57] ABSTRACT

A method of improving the endogenous production of prostaglandins by a mammal is disclosed which comprises administering to the mammal an effective amount of certain 1-pyridylalkyl-3-phenylthioureas. Disclosed also are novel substituted 1-pyridylalkyl-3-phenylthioureas and therapeutic compositions thereof which are useful in carrying out the method of the invention.

Disclosed also are methods of treating mammals for clinical conditions responsive to prostaglandins, such as for example, male infertility, epidermal injuries, atonic uterine bleeding, thromboembolic disease and like clinical conditions.

25 Claims, No Drawings

METHODS OF USE OF PYRIDYLALKYL PHENYLTHIOUREAS

CROSS-REFERENCE TO RELATED APPLICATIONS

This application is a continuation-in-part application of our co-pending application Ser. No. 428,373, filed Dec. 26, 1973, now abandoned.

BACKGROUND OF THE INVENTION

1. Field of the Invention

The invention is concerned with the production of endogenous prostaglandins by mammals and more specifically concerns a method of raising prostaglandin production levels in the mammal by administering 1-pyridylalkyl-3-phenylthioureas. The invention also concerns a novel group of substituted 1-pyridylalkyl-3-phenylthioureas and therapeutic compositions thereof.

2. Description of the Prior Art

Natural prostaglandins are a well-known group of physiologically active unsaturated hydroxy-substituted fatty acids which are biosynthesized endogenously by mammals such as, for example, canines, bovines, equines, swine, and humans. Identified roles of the natural prostaglandins in mammalian physiology are illustrated by their action as mediators in the inflammatory process, as tonal agents in effecting the contractility of smooth muscle and as activators in a wide variety of mammalian reproductive processes.

Structurally, the natural prostaglandins have been arbitrarily classified into four basic families termed "PGE", "PGF", "PGA", and "PGB", respectively. The various families are composed of differing analogs and stereoisomers having as a hypothetical parent structure, prostanoic acid. For example, the principal members of the PGE family are $11\alpha,15$-dihydroxy-9-keto-prosta-13-enoic acid (referred to alternatively for convenience as "$PGE_1$"), $11\alpha,15$-dihyroxy-9-keto-prosta-5,13-dienoic acid (hereinafter referred to alternatively as "$PGE_2$"); and $11\alpha$-15-dihydroxy-9-keto-prosta-5,13,17-trienoic acid (referred to alternatively for convenience as "$PGE_3$"). The principal members of the PGF family are $9\alpha,11\alpha,15$-trihydroxy-prosta-13-enoic acid (referred to alternatively for convenience as "$PGF_1\alpha$"); $9\beta,11\alpha,15$-trihydroxy-prosta-13-enoic acid (referred to alternatively for convenience as "$PGF_2\alpha$"); $9\beta,11\alpha,15$-trihydroxy-prosta-5,13-dienoic acid (referred to alternatively as "$PGF_2\beta$"); and $9\alpha,11\alpha,15$-trihydroxy-prosta-5,13,17-trienoic acid (referred to alternatively as "$PGF_3\alpha$").

Physiological activity of specific natural prostaglandin compounds may be the same, different in degree or differ from the physiologic activity of other specific natural prostaglandins. It appears, however, that they all share a common property in not being continually produced and released by the mammalian tissues of origin. Instead, the prostaglandins appear to be spontaneously synthesized in situ (biosynthesis being equivalent to release) in response to certain stimuli or "trigger" mechanisms. The prostaglandins generally exhibit an extremely short biological half-life and current knowledge indicates that there is no storage of prostaglandins by body tissues or fluids, with the possible exception of seminal fluids. It has been suggested that the trigger or stimulus for endogenous prostaglandin synthesis is associated with trauma of cellular membranes. Such trauma may occur through physical or chemical activity. For example, in the normal mammal carrying a fetus, circulating blood and amniotic fluids do not contain significant amounts of the prostaglandins $PGE_2$ and $PGF_2\alpha$ until birth is imminent. At that time the levels of $PGE_2$ and $PGF_2\alpha$ produced by placental and uterine tissues rise substantially. The suggested function of the prostaglandins at this stage of pregnancy is to stimulate uterine contractions, i.e., labor induction. As another example, injury to mammalian epidermal tissue triggers the in situ synthesis of $PGE_2$ at the site of injury. $PGE_2$ is known to promote and accelerate healing of epidermal wounds (see for example U.S. Pat. No. 3,711,515 at Column 5, lines 1–11).

We have discovered that the quantity of prostaglandins produced endogenously by a mammal following the stimulation of biosynthesis will be greatly enhanced, e.g., by from 5 to 10 percent to several times normal production, when certain 1-pyridylalkyl-3-phenylthioureas have been systemically administered to the mammal prior to the stimulation of biosynthesis by normal trigger mechanisms.

Prior to our invention there was a suggestion that thrombin caused by an increase in the production levels of $PGE_2$ and $PGF_2\alpha$ in mammalian blood platelets (Smith et al., Nature New Biol., 231, 235).

Prior to our invention the treatment of clinical conditions responsive to the presence of prostaglandins had been limited to the administration of prostaglandins from exogenous sources. The method of our invention has a number of advantages over the administration of exogenous prostaglandins. For example, as mentioned above, the biological half-life of the naturally occurring prostaglandins is extremely short. Illustratively, it has been reported that after about 20 minutes, 500 $\mu$g. of $PGF_2\alpha$ administered intravenously to an adult human cannot be detected in the body. Therefore, to treat clinical conditions such as an epidermal injury with exogenous sources of prostaglandins, it is necessary to employ a continuous administration of the desired prostaglandin over a prolonged period of time. By our method, therapeutic levels of the desired prostaglandin are delivered at the "target site" or site of injury with maximum efficiency. Sustained high levels of prostaglandin are observed for several hours following treatment according to our method thus eliminating the need for continuous exogenous prostaglandin administration over long periods of time. In addition the systemic administration of exogenous prostaglandins delivers the prostaglandin to organs and tissues other than those at the desired target site. This may result in undesirable responses or "side-effects". By the method of our invention, therapeutic levels of natural prostaglandins are produced at the target site, i.e., at the point of epidermal injury or at the locality stimulating synthesis. This reduces the likelihood of response in remotely located tissues, minimizing side-effects.

Prior hereto, 1-(2-pyridylethyl)-3-phenyl-2-thiourea was known; see Sheob et al., Indian J. Chem., 5, 145, (1967). Also known were the 1-(2-pyridylmethyl)-3-(fluorophenyl)-2-thioureas; see Xuong et al., Med. Exp. 10, 272–6, (1964) and the 1-(pyridylmethyl)-3-phenylureas; see U.S. Pat. No. 3,700,678. Adkins et al., J. Am. Chem. Soc., 66, 1293, (1944) disclosed a 1-(pyridylalkyl-3-phenyl-2-thiourea and Novikov, Khim. Geterotsikl Soedin, (1), 115-6, (1968) described 1-ethyl-1-(4-pyridylmethyl)-3-naphthyl-2-thiourea. Murashova et al., Zh. Anal. Khim., 24, 1205, (1969) disclosed a number of thioureas including 1-(pyridylethyl)-1-naphthyl-3-phenyl-2-thiourea.

SUMMARY OF THE INVENTION

The invention comprises a method of increasing the production of endogenous prostaglandins by a mammal which comprises administering to said mammal an effective amount of a compound selected from those of formula:

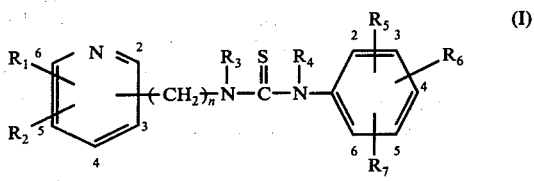

pyridyl N-oxides thereof and pharmaceutically acceptable acid addition salts thereof wherein $R_1$ and $R_2$ are each selected from hydrogen, halogen, hydrocarbyl having 1 to 6 carbon atoms, inclusive, alkoxy, alkylthio, nitro, amino, alkylamino, dialkylamino, acylamino and trihalomethyl; $R_3$ and $R_4$ are each selected from hydrogen, lower alkyl, cycloalkyl, aryl, aralkyl and aryl substituted with a group selected from halogen, lower alkoxy; halogen substituted lower alkyl and halogen-substituted lower alkoxy, $R_5$ is selected from hydrogen, halogen, hydrocarbyl, alkoxy and halogen-substituted hydrocarbyl; $R_6$ and $R_7$ are each selected from nitro, cyano, amino, acylamino, alkylamino, dialkylamino, alkylthio, arylthio, aryloxy and a group $R_5$ as previously defined; and $n$ is an integer of from 1 to 2, inclusive.

Preferred for carrying out the method of the invention are those compounds (I) having the more specific formula:

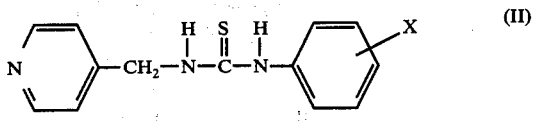

pyridyl N-oxides thereof and pharmaceutically acceptable acid addition salts thereof wherein X is selected from hydrogen, halogen, nitro, cyano and trihalomethyl.

The invention also comprises novel compounds within the scope of formula (I) and having the formula (I) provided that when $R_1$, $R_2$, $R_4$, $R_5$, $R_6$ and $R_7$ are each hydrogen, said compound is selected from those wherein $R_3$ is selected from lower alkyl, cycloalkyl, aralkyl, aryl and aryl substituted with a group selected from halogen, lower alkoxy, halogen-substituted lower alkyl and halogen-substituted lower alkoxy; and further provided that when one of $R_5$, $R_6$ and $R_7$ is selected from halogen and alkoxy then $R_3$ is selected from lower alkyl, cycloalkyl, aryl, aralkyl and aryl substituted with a group selected from halogen, lower alkoxy, halogen-substituted lower alkyl and halogen-substituted lower alkoxy, and the pharmaceutically acceptable acid addition salts thereof.

Preferred novel compounds for use in the method of the invention are those of the more specific formula:

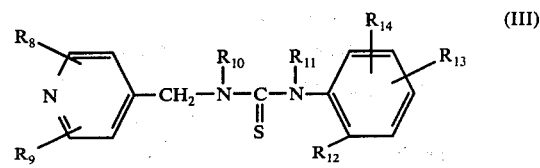

and the pharmaceutically acceptable acid addition salts thereof wherein $R_8$ and $R_9$ are selected from the group consisting of hydrogen, halogen, hydrocarbyl of 1 to 6 carbon atoms, inclusive, and trihalomethyl;

$R_{10}$ and $R_{11}$ are each selected from hydrogen, lower alkyl, cycloalkyl and phenyl; $R_{12}$, $R_{13}$ and $R_{14}$ are each selected from hydrogen, halogen, hydrocarbyl, halogen-substituted hydrocarbyl, cyano, alkoxy and alkylthio; provided that when $R_8$, $R_9$, $R_{11}$, $R_{12}$, $R_{13}$ and $R_{14}$ are each hydrogen then $R_{10}$ is selected from lower alkyl, lower cycloalkyl and phenyl; and further provided that when one of $R_{12}$, $R_{13}$ and $R_{14}$ is selected from halogen and alkoxy then $R_{10}$ is selected from lower alkyl, lower cycloalkyl and phenyl.

The term "halogen" is used herein in its conventional sense as embracive of chlorine, bromine, fluorine, and iodine and the term "halo" means chloro, bromo, fluoro and iodo, respectively.

The term "hydrocarbyl" is used through the specification and claims as meaning the monovalent moiety obtained by removal of a hydrogen atom from a parent hydrocarbon, which latter contains 1 to 12 carbon atoms. Illustrative of such moieties are alkyl of 1 to 12 carbon atoms, inclusive, such as methyl, ethyl, propyl, butyl, pentyl, hexyl, heptyl, octyl, nonyl, decyl, undecyl, dodecyl and isomeric forms thereof; cycloalkyl of 3 to 8 carbon atoms, inclusive, such as cyclopropyl, cyclobutyl, cyclopentyl, cyclohexyl, cycloheptyl, cyclooctyl, and the like; alkenyl of 2 to 12 carbon atoms, inclusive; such as vinyl, allyl, butenyl, pentenyl, hexenyl, heptenyl, octenyl, nonenyl, decenyl, undecenyl, dodecenyl and isomeric forms thereof; aryl of 6 to 12 carbon atoms, inclusive, such as phenyl, tolyl, xylyl, napthyl, biphenylyl and the like, aralkyl of 7 to 12 carbon atoms, inclusive, such as benzyl, phenethyl, phenpropyl, phenbutyl, phenpentyl, phenhexyl and the like.

The terms alkyl, alkenyl, cycloalkyl, aryl and aralkyl, as used in this application, are as defined in the above paragraph.

The term "halogen-substituted hydrocarbyl" means hydrocarbyl as defined above wherein one or more hydrogen atoms have been replaced with a halogen atom as defined above. Illustrative of halogen-substituted hydrocarbyl are trichloromethyl, bromocyclobutyl, 1,2-diiodovinyl, chlorophenyl, p-chlorobenyl and the like.

The term "alkoxy" is used herein to mean the monovalent moiety of the formula:

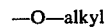

wherein alkyl is as described above. Illustrative of alkoxy are methoxy, ethoxy, butoxy, pentyloxy, heptyloxy, decyloxy, dodecyloxy, and the like.

The term "alkylthio" means the monovalent moiety of formula:

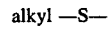

wherein alkyl is as previously defined. Representative of alkylthio are methylthio, pentylthio, dodecylthio and the like.

The term "arylthio" as used herein means the monovalent moiety of formula:

aryl —S— wherein aryl is as defined above. Illustrative of arylthio are phenylthio, naphthylthio and the like.

The term "dialkylamino" is used to mean an amino group wherein both hydrogen atoms have been replaced with alkyl groups as defined above. Illustrative of dialkylamino are groups such as dimethylamino, ethylhexylamino, didodecylamino and the like.

The term "alkylamino" is used herein to mean an amino group wherein one hydrogen has been replaced with an alkyl group as previously defined. Illustrative of alkylamino are methylamino, butylamino, dodecylamino and the like.

The term "acylamino" as used herein means the monovalent moiety of formula:

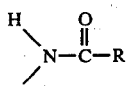

wherein R is alkyl as previously defined.

The term "lower alkyl" means alkyl as previously described having 1 to 4 carbon atoms, inclusive. The term "lower cycloalkyl" means cycloalkyl as previously described having 3 to 6 carbon atoms, inclusive, and the term "lower alkoxy" means alkoxy as defined above having 1 to 4 carbon atoms, inclusive.

The term "halogen-substituted lower alkyl" means lower alkyl as defined above wherein one or more of the hydrogen atoms have been replaced with halogen as previously defined. Illustrative of such groups are chloromethyl, trifluoromethyl, 1,2-dibromoethyl, 1,1,3,3-tetrachloropropyl and the like.

The term "halogen-substituted lower alkoxy" means lower alkoxy as defined above, wherein one or more hydrogen atoms have been replaced with a halogen atom. Illustrative of such halogen-substituted groups are 1-chloroethoxy, 1,2-dibromobutoxy, and the like.

One skilled in the art will appreciate a variety of useful procedures which may be carried out by using the method of our invention. For example, natural prostaglandins are sought after for biological studies, and as therapeutics in the treatment of mammals By the method of our a variety of clinical conditions. The extraction and recovery of natural prostaglandins from animal tissues such as mammalian lung tissue, male accestory genital glands and the like from sacrificed animals is a costly procedure and any improvement of yields is a significant commercial factor. By the method of our invention, effective amounts of compounds of the formula (I) are administered to the natural prostaglandin producing animal within a period of from 1 to about 6 hours prior to sacrifice. This results in enhanced yields of prostaglandins recovered by the conventional and known methods of extraction.

By the method of our invention, mammal treatment procedures for a variety of clincial conditions responsive to prostaglandins are improved. More specifically, those clinical conditions which are related to a prostaglandin deficiency or which respond to enhanced levels of prostaglandins and in which there is an operative trigger mechanism for stimulation of prostaglandin production are advantageously responsive to the method of our invention. Illustratively, some 13 different prostaglandins, representing all four prostaglandin families, are found in mammalian seminal fluids. A correlation exists between low prostaglandin levels (particularly of the PGE family) in seminal fluids and male infertility; see for example "The Prostaglandins", Karim, Medical and Technical Pub. Co. Ltd., Oxford (1972) pp. 134–6. In those instances wherein seminal fluid prostaglandins are produced by the mammal, but in low quantity, production levels are raised by the method of our invention. Thus, the method of our invention provides a method of treating mammalian male infertility which comprises administering to said male an effective amount of a compound (I) or a pyridyl N-oxide or a pharmaceutically acceptable acid addition salt thereof.

To further illustrate the use of the method of our invention, it is known that the prostaglandin $PGE_2$ is produced at the site of epidermal injury in a mammal [see for example Anggard et al., Alza Conference on Prostaglandins in Cellular Biology, Edited by Ramwell and Pharriss, Plenum Press, N.Y., N.Y. (1972) at page 269]. The generally accepted role of $PGE_2$ at the site of injury following, for example, burns, abrasions, surgery, penetration wounds and like epidermal injuries is to stimulate epidermal cell proliferation and keratin formation, thereby accelerating wound healing. It should be further noted that the term "epidermal injury" is broad enough in this context to include skin conditions such as psoriasis wherein the $PGE_2$ stimulates production of cyclic AMP which additionally aids in overcoming the effects of the condition. By using the method of our invention, higher levels of $PGE_2$ are obtained over longer periods of time to accelerate the healing process. Thus, a preferred embodiment of the method of our invention comprises a method of promoting the healing of epidermal injuries in a mammal which comprises administering to said mammal an effective amount of a compound selected from those of the formula (I), pyridyl N-oxides thereof and pharmaceutically acceptable acid addition salts thereof. Surprisingly, although $PGE_2$ is a known mediary in the inflammatory process, the method of our invention so employed does not produce a significant increase in the manifestations generally associated with inflammation such as pain, edema, swelling and the like.

In another use, the method of our invention is employed advantageously to prevent or control atonic uterine bleeding. $PGE_2$ and $PGF_2\alpha$ are both produced by the endometrium and blood platelets (upon aggregation). In situations of post-partum hemorrhage due to an atonal uterus, the elevation of $PGE_2$ and $PGF_2\alpha$ production by platelets at the site of bleeding provides therapeutic levels of the two prostaglandins sufficient to render tone to the uterine muscle, thus causing sustained contraction of the uterus and controlling hemorrhage. The method of our invention therefore includes as an embodiment the prevention and control of atonic uterine hemorrhage in a mammal which comprises administering to the mammal an effective amount of a compound selected from those of formula (I), pyridyl N-oxides thereof and pharmaceutically acceptable acid addition salts thereof. Administration of the compound (I), its N-oxides or its salts in this particular use is advantageously carried out during a period of from 1 to about 6 hours before an anticipated hemorrhage to prevent the same, or immediately following the start of hemorrhage. In the latter instance, control generally occurs within from 1 to about 3 hours of administration.

As mentioned above, $PGF_2\alpha$ and $PGE_2$ are produced by the mammalian blood platelet upon stimulation of synthesis by cell aggregation. Build-up of $PGF_2\alpha$ and $PGE_2$ levels at the site of platelet aggregation are associated with inhibition of further platelet aggregation, thereby terminating the continued development of thrombi. By the method of our invention, one may terminate the development of thrombi earlier and more rapidly through enhanced levels of $PGF_2\alpha$ production. This is particularly useful in the treatment and prevention of myocardial infarcts, post-operative thrombosis, atherosclerosis, arteriosclerosis and like clinical conditions where the development of a thrombus is undesired. Thus, another embodiment of our invention comprises a method of controlling the development of a thrombus in a mammal which comprises administering an effective amount of a compound selected from those of formula (I), pyridyl N-oxides thereof and pharmaceutically acceptable acid addition salts thereof, to said mammal.

DETAILED DESCRIPTION OF THE INVENTION

The compounds (I), pyridyl N-oxides thereof and pharmaceutically acceptable acid addition salts thereof are administered to the mammal systemically and topically. Illustrative of the systemic methods of administration are oral and parenteral. However, a systemic effect can be achieved through a topical administration, such as a rectal suppository. Topical compositions can be used for treating epidermal injury such as psoriasis.

The effective amount of compounds (I), their N-oxides and salts thereof administered is that quantity which brings about an increase in the production levels of prostaglandins biosynthesized by the subject mammal. The exact amount administered will depend upon a number of factors such as, for example, the specific compound (I), its N-oxide or salt, species of mammal, age, weight, sex and physical condition of the mammal, route of administration and in the instances wherein a specific clinical condition is being treated by the method of the invention, the nature of the condition. In general, prostaglandin production levels rise in direct proportion to the quantity of the compound (I) administered.

The exact dosage requirement for increasing prostaglandin production in a given situation may be determined by administration of a trial dose and observation of the prostaglandin production response by blood plasma analysis and by clinical response to the presence of prostaglandins. In general, an effective amount to be administered is within the range of from about 0.1 to about 500 mg. per kilogram of body weight of the recipient mammal and preferably within the range of from about 5 to about 50 mg. per kilogram body weight. In general, the degree of response is related to dose, and higher doses produce faster and more complete clinical responses. In most instances, a single administration will effect the desired response and bring about the result desired. In cases such as the treatment of epidermal injuries, however, it may be desirable to repeat the administrations several times. In instances of repeated administration, we have noted a decrease in degree of prostaglandin production response upon administrations subsequent to the first unless there is a resting period between administrations. Resting periods of from about 12 to about 24 hours between administrations assure the highest prostaglandin production for a given dosage of the compounds (I), their N-oxides and pharmaceutically acceptable acid addition salts.

Although all mammalian tissues capable of producing prostaglandins are responsive to the method of our invention, the most advantageous response is obtained from circulating blood platelets which produce $PGE_2$ and $PGF_2\alpha$. The platelets produce larger quantities of these prostaglandins and serve to meet therapeutic needs as described above most readily and conveniently. The method of our invention is particularly advantageous in stimulating high yields of $PGF_2\alpha$ from the producing blood platelets.

Illustrative of the known compounds of formula (I) employed in the method of our invention are 1-(2-pyridylethyl)-3-phenyl-2-thiourea, 1-(2-pyridylmethyl)-3-(3-fluorophenyl)-2-thiourea and the like.

The compounds of formula (I) are readily prepared by a variety of methods well known in the art; see, for example, A. Shoeb, et al., *Indian J. Chem.* 5, 145 (1967). In general, those compounds (I) wherein $R_4$ is specifically hydrogen and $R_6$ and $R_7$ are as defined above but other than amino or alkylamino may be prepared by reacting together substantially equimolar proportions of the appropriate phenyl isothiocyanate (V) and the appropriate aminoalkylpyridine (IV) according to the schematic formula:

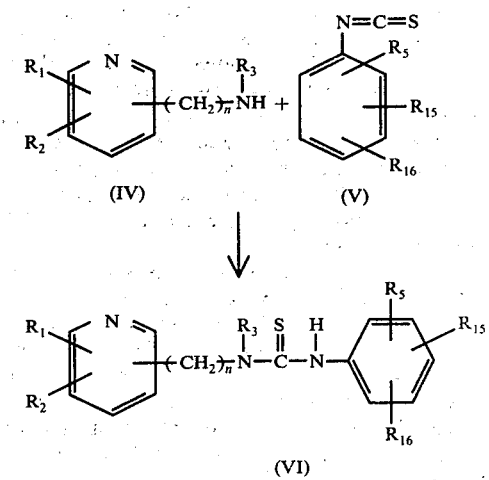

where $R_1$, $R_2$, $R_3$, $R_5$ and $n$ are as defined above; $R_{15}$ and $R_{16}$ are each selected from nitro, cyano, dialkylamino, acylamino, alkylthio, arylthio, aryloxy and a group $R_5$ as defined previously.

The reaction illustrated above proceeds satisfactorily in the presence of an inert organic solvent. By an inert organic solvent we mean an organic solvent which does not react with or in any way interfere with the desired course of the reaction. Illustrative of inert organic solvents are tetrahydrofuran, dioxane, benzene, pyridine and the like.

The reaction my be carried out over a broad range of temperature, i.e., from about 0° C. to reflux temperature. The length of time required to carry out the reaction is generally dependent upon the nature of the groups $R_1$, $R_2$, $R_3$, $R_4$, $R_5$, $R_{15}$ and $R_{16}$ and the temperature employed. Completion of the reaction may be observed by conventional analtyical methods such as by infra-red spectral analysis and thin-layer chromatography which will show the disappearance of the isothiocyanate reactant (V) of the desired products of formula (VI).

Upon completion of the reaction, the desired product (VI) is readily separated from the reaction mixture by conventional methods, i.e., by stripping solvent, filtration, recrystallization and like techniques.

The starting aminoalkylpyridine compounds (IV) employed in the above described reaction are generally well known and may be prepared by a variety of methods; see, for example, Sculley et al., J. Am. Chem. Soc., 75, 3400 (1973); Shuman et al., J. Org. Chem., 27, 1970 (1962); Bobbitt et al., J. Org. Chem., 29, 2298 (1964); Bower et al., J. Chem. Soc., 2834 (1955); Bruce et al., J. Am. Chem. Soc., 66, 2092 (1944); and Sam, J. Pharm. Science, 56, 1202 (1967).

A convenient method of preparing the aminoalkylpyridines (IV) wherein $R_1$ and $R_2$ are other than acylamino groups is by reduction of the corresponding amide compounds of formula:

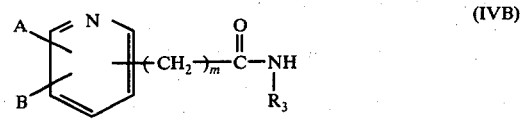 (IVB)

wherein $m$ is an integer of from 0 to 1 and $R_3$ is as defined above; A and B are each selected from hydrogen, halogen, hydrocarbyl of 1 to 6 carbons, inclusive, alkoxy, alkylthio, nitro, amino, alkylamino, dialkylamino, and trihalomethyl. The methods of reduction are well known, see for example, Tarbell et al., J. Am. Chem. Soc., 72, 2657 (1950); Uffer et al., Helv. Chim. Acta., 31, 1397 (1948); and Brown, Org. Reactions, Vol. 6., J. Wiley and Sons, N.Y., N.Y., (1951), page 469.

Representative of the compounds (IVB) are N-ethyl-2,6-dimethylisonicotinamide, 2-chloro-6-ethylthioisonicotinamide, N-butyl-2-ethylthioisonicotinamide, N-butyl-2,6-dichloroisonicotinamide, 2-chloro-6-methoxy-N-(α-methylphenylethyl)isonicotinamide, N-benzyl-4-pyridylacetamide, 2-pyridineacetanilide, 4'-phenoxynicotinanilide, 2'-phenylnicotinanilide, 5'-methyl-4'-nitro-o-picolinanisidide, 4'-cyclohexynicotinanalide, N-1-naphthylisonicotinamide, 4'-chloroisonicotinanilide, p-isonicotinanisidene, 2'-chloro-4'-nitropicolinanilide and 2',5'-diethoxy-4'-nitropicolinanilide, N-[3-(o-chlorophenyl)propyl]isonicotinamide, N-cyclopropylisonicotinamide, 2,6-dichloro-N-(cyclopropylmethyl)isonicotinamide, N-(diphenylmethyl)isonicotinamide, N-butyl-6-methylthiopicolinamide, N-cyclohexylpicolinamide, 4,6-dichloropicolinamide, 4-ethoxypicolinamide, 5-ethylthiopicolinanilide, and the like.

An alternative method of preparing the aminoalkylpyridines (IV) wherein $R_3$ is specifically hydrogen and a method for preparing compounds (IV) wherein $R_1$ and/or $R_2$ are acylamino groups is that disclosed by Sculley et al., supra. which comprises reducing the corresponding nitrile compounds of formula:

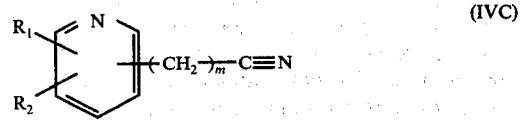 (IVC)

wherein $R_1$, $R_2$ and $m$ are as before defined. Represenative of the compounds (IVC) are picolinonitrile, 4-chloropicolinonitrile, 3,6-dichloropicolinonitrile, 4-methylpicolinonitrile, 4,6-dimethylpicolinonitrile, 4-phenylpicolinonitrile, 4-benzylpicolinonitrile, 3-allylpicolinonitrile, 4-methoxypicolinonitrile, 2,5-diethoxypicolinonitrile, 4-methylthiopicolinonitrile, 3,5-dinitropicolinonitrile, 3,5-diaminopicolinonitrile, 3-ethylaminopicolinonitrile, 3-diethylaminopicolinonitrile, 4-acetylaminopicolinonitrile, 4-trifluoromethylpicolinonitrile, 3-pyridylacetonitrile and the like.

Those compounds (IV) wherein $R_1$ and/or $R_2$ are acylamino groups may also be prepared by N-acylation of the corresponding compounds (IV) wherein $R_1$ and/or $R_2$ are amino groups. The methods of such N-acylations are well known, such as by reaction of the appropriate compounds (IV) with an appropriate acyl halide of formula:

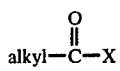

wherein alkyl and X are as defined above.

Phenylisothiocyanates of formula (V) are generally well known as illustrated by phenylisothiocyanate, p-chlorophenylisothiocyanate, p-methylphenylisothiocyanate, p-phenylphenylisothiocyanate, m-ethoxyphenylisothiocyanate, p-(3,5-dichlorophenyl)phenylisothiocyanate, o-nitrophenylisothiocyanate, m-cyanophenylisothiocyanate, o-diethylaminophenylisothiocyanate, p-ethylthiophenylisothiocyanate, p-phenylthiophenylisothiocyanate, p-phenoxyphenylisothiocyanate and the like.

Those compounds (I) wherein $R_3$ is specifically hydrogen and $R_1$ and $R_2$ are as previously defined but other than amino or alkylamino are prepared by the above-described method for preparing the compounds (VI) but by replacing the aminoalkylpyridine (IV) as used therein with an appropriate substituted pyridylalkylisothiocyanate of formula:

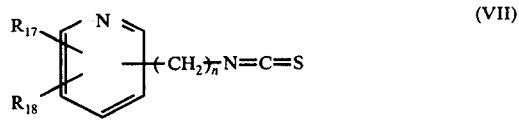 (VII)

wherein $n$ is as previously defined; $R_{17}$ and $R_{18}$ are each selected from hydrogen, halogen, hydrocarbyl of 1 to 6 carbon atoms, inclusive, alkoxy, alkylthio, nitro, dialkylamino, acylamino and trihalomethyl; and in conjunction therewith, replacing the phenylisothiocyanate (V) as used therein with an appropriate aniline of formula:

 (VIII)

wherein $R_4$, $R_5$, $R_6$ and $R_7$ are as previously defined.

Pyridylalkylisothiocyanates of formula (VII) are prepared by thiophosgenation of the corresponding pyridylalkylamine such as those within the scope of the formula (IV), supra. The method of thiophosgenation of such amines is well known; see for example, Dyson, Organic Synthesis, Coll. Vol. 1, 2nd Ed., Wiley, N.Y., N.Y., 1946, pg. 165 and U.S. Pat. No. 2,905,701.

Illustrative of the compounds (VII) are 2-pyridylmethylisothiocyanate and the heterocyclic isothiocyanates disclosed in U.S. Pat. No. 2,905,701.

Anilines of the formula (VIII) are generally well known and are illustrated by aniline, p-chloroaniline, 2,5-dibromoaniline, 3,4,5-trichloroaniline, m-toluidine, 3,5-dibutylaniline, 3-allylaniline, p-phenylaniline, p-benzanilide, m-phenetidine, 3,4,5-trimethoxyaniline, m-dichloromethylaniline, p-(p-chlorphenyl)aniline, p-nitroaniline, m-cyanoaniline, p-phenylenediamine, p-acetylaminoaniline, o-methylaminoaniline, o-dimethylaminoaniline, 2,5-dimethylthioaniline, p-phenylthioaniline, p-phenoxyaniline, o-(2-chloroethyl)aniline, 4-(methylthio)aniline, 3-(ethylthio)-4-(methylthio)aniline, 4-bromo-2-chloroaniline, 2-bromo-4,6-dinitroaniline, 2-bromo-4-methylaniline, 2-bromo-4-nitroaniline, 3-chloro-o-anisidine, 5-chloro-2,4-dimethoxyaniline, 4-fluoro-3-nitroaniline, p-(2,2,2-trichloroethyl)aniline, N-methylaniline, N-cyclohexylaniline, N-phenylaniline, N-benzylaniline and the like.

Those compounds (I) wherein $R_1$, $R_2$, $R_6$ or $R_7$ are specifically selected from amino, alkylamino and acylamino, may also be prepared from the corresponding compounds (I) wherein $R_1$, $R_2$, $R_6$ and/or $R_7$ are nitro groups. Thus by conventional methods of reduction [see for example the method of Pietra, Ann. Chim., 45, 850 (1955)], the nitro substituent group is reduced to an amino group; and by conventional methods well known in the art, such as by reaction with an appropriate alkyl halide of formula:

alkyl—Y wherein Y represents halogen, the primary amino groups may be converted to alkylamino groups [see for example the method of Johnstone, et al., J. Chem. Soc., (C), 2223 (1969)]. When desired, conversion of the substituent amino group to an acylamino group is also carried out by conventional and known methods such as by reaction with an appropriate acid anhydride or acyl chloride such as those of the formula:

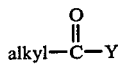

where Y is as defined above and alkyl is as defined previously.

The pyridyl N-oxides of the compounds (1), i.e., compounds of the formula:

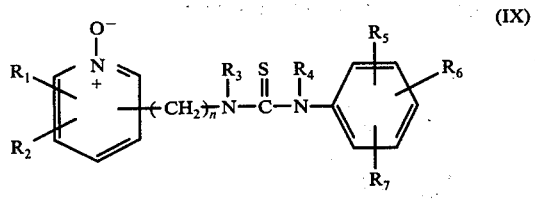

(IX)

and the pharmaceutically acceptable acid addition salts thereof wherein $R_1$, $R_2$, $R_3$, $R_4$, $R_5$, $R_6$, $R_7$ and $n$ have the meanings previously ascribed to them are also novel compounds and are useful for the same purposes and in the same manner as the non-oxides of formula (1).

The pyridyl N-oxides (IX) are prepared by N-oxidation of the corresponding compound (1). Such oxidations are well known, and are generally carried out by reacting the compound (1) with an excess molar proportion of an oxidizing agent such as hydrogen peroxide. See for example the procedure disclosed in E. Ochiai, *Aromatic Amino Oxides*, Elsevier Pub. Co., New York, Pg. 25 (1967).

The pharmaceutically acceptable acid addition salts of the compound (1) and compounds (IX) may be used for the same purposes as the corresponding free base compounds, and in the same manner. They are readily prepared by reacting the free base with a stoichiometric proportion of an appropriate acid. The method is well known to those skilled in the art and may be carried out in aqueous or non-aqueous media such as ethanol, ether, ethyl acetate and the like. Illustrative of pharmaceutically acceptable acid addition salts are those formed upon reaction of the free base compound (1) or compound (IX) with hydrochloric acid, hydrobromic acid, sulfuric acid, phosphoric acid, acetic acid, lactic acid, citric acid, succinic acid, benzoic acid, salicyclic acid, pamoic acid, cyclohexanesulfamic acid and the like.

This invention relates also to pharmaceutical dosage unit forms for systemic and topical administration which are useful in improving the production of endogenous prostaglandins by mammals, including humans. Preferred as the modes of administration are oral and parenteral. The term "dosage unit form" as used in this specification and in the claims refers to physically discrete units suitable as unitary dosages for mammalian subjects, each unit containing a predetermined quantity of the essential active ingredient, i.e., a compound of formula (IX); or a compound of the formula (1) wherein it is provided that when $R_1$, $R_2$, $R_4$, $R_5$, $R_6$ and $R_7$ are each hydrogen, said compound (1) is selected from those wherein $R_3$ is selected from lower alkyl, cycloalkyl, aralkyl, aryl and aryl substituted with a group selected from halogen, lower alkoxy, halogen-substituted lower alkyl and halogen-substituted lower alkoxy; and further provided that when one of $R_5$, $R_6$ and $R_7$ is selected from halogen and alkoxy then $R_3$ is selected from lower alkyl, cycloalkyl, aryl, aralkyl and aryl substituted with a group selected from halogen, lower alkoxy, halogen-substituted lower alkyl and halogen-substituted lower alkoxy; or pharmaceutically acceptable acid addition salts thereof, calculated to produce the desired effect in combination with the required pharmaceutical means which adapt said ingredient for systemic administration. Examples of dosage unit forms in accordance with this invention are tablets, capsules, orally administered liquid preparations in liquid vehicles, sterile preparations in liquid vehicles, sterile preparations in liquid vehicles for intramuscular and intravenous administration, suppositories and sterile dry preparations for the extemporaneous preparation of sterile injectable preparation in a liquid vehicle. Solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn syrup, corn starch, talc and the like. Capsules, both hard and soft, are formulated with conventional diluents and excipients, for example, edible oils, talc, calcium carbonate, calcium stearate and the like. Liquid preparations for oral administration are prepared in water or aqueous solutions which advantageously contain suspending agents such as, for example, carboxymethylcellulose, methylcellulose, acacia, polyvinyl pyrrolidone, polyvinyl alcohol and the like. In the instance of injectable forms, they must be sterile and must be fluid to the extent that easy syringeability exists. Such preparations must be stable under the conditions of manufacuture and storage, and ordinarily contain in addition to the basic solvent or suspending liquid, preservatives in the nature of bactericidal and fungicidal agents, for example, parabens, chlorobutanol, benzyl alcohol, phenol, thimerosal, and the like. In many cases it is preferable to include isotonic agents, for example, sugars or sodium chloride. Carriers and vehicles include vegetable oils, ethanol and polyols, for example, glycerol, propylene glycol, liquid polyethylene glycol and the like. Any solid preparations for subsequent extemporaneous preparation of sterile injectable preparations are sterilized, preferably by exposure to a sterilizing gas such as, for example, ethylene oxide. The aforesaid carriers, vehicles, diluents, excipients, preservatives, isotonic agents and the like constitute the pharmaceutical means which adapt the preparations for systemic administration.

For topical use, this compound can be formulated in a pharmaceutical carrier suitable for application to affected areas of the skin, eyes, ears or mucous membranes. Accordingly, the compositions of this invention include those pharmaceutical forms in which the medication is applied externally for direct contact with the surface to be treated. Conventional pharmaceutical forms for this purpose include ointments, creams, lotions, solutions, suspensions, pastes, jellies, sprays and aerosols (e.g. for oral or nasal use or on the skin), drops (e.g. for use in the eyes or ears), powders (e.g. for use on the skin) and the like. In preparing the desired topical formulations of the novel compound of this invention, various additives, diluents and adjuvants can be utilized. These illustratively include water, surfactants (e.g., polysorbate 80 and polyoxyethylene sorbitan monostearate), emulsifiers (e.g., glyceryl monostearate-diethylaminoethyl alkyl amide phosphate, isopropyl myristate and cetyl alcohol), alcohols (e.g., ethanol and isopropanol), lower alkyl diols (e.g., 1,3-butanediol, 2,3-butanediol, 1,2-propanediol, 1,3-propanediol), glycols (e.g., propylene glycol, glycerol, sorbitol), ointment-type bases (e.g., spermaceti, Carbowaxes, beeswax, petrolatum, lanolin), higher fatty acids and alcohols (e.g., stearic acid, stearyl alcohol, cetyl alcohol, palmitic acid), liquid paraffin and vegetable oils (e.g., peanut oil, castor oil), preservatives such as sorbic acid, parabens, chlorocresol, benzalkonium chloride) and solid diluents (e.g., lactose, starch, benonite, talc).

A rectal suppository can be employed to deliver the active compound where the mammal cannot be treated conveniently by means of other dosage forms, such as orally, as in the case of young children or debilitated persons. The active compound can be incorporated into any of the known suppository bases by methods known in the art. Examples of such bases include cocoa butter, polyethylene glycols (Carbowaxes), polyethylene sorbitan monostearate, and mixtures of these with other compatible materials to modify the melting point or dissolution rate. These rectal suppositories can weigh from about 1 to about 2.5 Gm.

The pharmaceutical dosage unit forms are prepared in accordance with the preceding general description to provide from about 10 to about 1500 mg. of the essential active ingredient per dosage unit form with preferably oral from about 100 to about 1000 mg. and parenterally, i.e., intramuscularly, about 50 to about 500 mg. Topical compositions from about 1 to about 15 weight percent can be employed.

The following examples describe the manner and process of making and using the invention, and set forth the best mode contemplated by the inventors of carrying out the invention but are not to be construed as limiting.

EXAMPLE 1

1-(p-cyanophenyl)-3-(4-pyridylmethyl)-2-thiourea

To a mixture of 3.25 gms. (0.03 mole) of 4-aminomethylpyridine and 100 ml. of tetrahydrofuran there is slowly added with stirring 4.81 gms. (0.03 mole) of p-cyanophenylisothiocyanate. Upon completion of addition, the reaction mixture is allowed to stand for 23 hours at ambient temperatures and then it is refluxed for 10 minutes. Solvent is removed under vacuum and the residue crystallized from a mixture of acetone and water (4:1 v/v) to give 5.8 gms. (72 percent of theory) of 1-(p-cyanophenyl)-3-(4-pyridylmethyl)-2-thiourea in the form of pale yellow granules, M. P. 168.7° C.

Similarly, following the above procedure but replacing the p-cyanophenylisothiocyanate as used therein with an equal molar proportion of p-tolylisothiocyanate, m-methoxyphenylisothiocyanate, p-acetamidophenylisothiocyanate, o-diethylaminophenylisothiocyanate, and p-methylthiophenylisothiocyanate, respectively, there is obtained 1-(p-tolyl)-3-(4-pyridylmethyl)-2-thiourea, 1-(m-methoxyphenyl)-3-(4-pyridylmethyl)-2-thiourea, 1-(p-acetamidophenyl)-3-(4-pyridylmethyl)-2-thiourea, 1-(o-diethylaminophenyl)-3-(4-pyridylmethyl)-2-thiourea and 1-(p-methylthiophenyl)-3-(4-pyridylmethyl)-2-thiourea, respectively.

EXAMPLE 2

1-(p-nitrophenyl)-3-(4-pyridylmethyl)-2-thiourea

Following the procedure of Example 1., supra., but replacing the p-cyanophenylisothiocyanate as used therein with an equal molar proportion of p-nitrophenylisothiocyanate there is obtained 7.13 gms. (83 percent of theory) of 1-(p-nitrophenyl)-3-(4-pyridylmethyl)-2-thiourea in the form of yellow granules, M. P. 173.2° C.

EXAMPLE 3

1-(4-pyridylmethyl)-3-(trifluoromethylphenyl)-2-thiourea

Following the procedure of Example 1., supra., but replacing the p-cyanophenylisothiocyanate as used therein with an equal molar proportion of 3-trifluoromethylphenylisothiocyanate there is obtained 6.12 gms. (66 percent of theory) of 1-(4-pyridylmethyl)-3-(3-trifluoromethylphenyl)-2-thiourea in the form of yellow crystals, M. P. 128.6° C.

EXAMPLE 4

1-(p-fluorophenyl)-3-(4-pyridylmethyl)-2-thiourea

Following the procedure of Example 1., supra., but replacing the p-cyanophenylisothiocyanate as used therein with an equal molar proportion of p-fluorophenylisothiocyanate there is obtained 5.45 gms. (70 percent of theory) of 1-(p-fluorophenyl)-3-(4-pyridylmethyl)-2-thiourea in the form of brown crystals, M. P. 166.3° C.

EXAMPLE 5

1-(m-fluorophenyl)-3-(4-pyridylmethyl)-2-thiourea

Following the procedure of Example 1., supra., but replacing the p-cyanophenylisothiocyanate as used therein with an equal molar proportion of m-fluorophenylisothiocyanate there is obtained 4.54 gms. (58 percent of theory) of 1-(m-fluorophenyl)-3-(4-pyridylmethyl)-2-thiourea in the form of brown crystals, M.P. 148.4° C.

Similarly, following the above procedure but replacing the 4-aminomethylpyridine as used therein with an equal molar proportion of 2-aminomethyl-6-methylpyridine, 2-(2-aminoethyl)-5-ethylpyridine, 3-amino-5-(aminomethyl)-2-methylpyridine, 2-(aminomethyl)-3-chloropyridine, 2-(aminomethyl)-4-phenylpyridine, 2-(aminomethyl)-4-benzylpyridine, 2-(aminomethyl)-4-methoxypyridine, 2-(aminomethyl)-4-methylthiopyridine, 2-aminomethyl)-3-nitropyridine, 2-(aminomethyl)-3-ethylaminopyridine, 2-(aminomethyl)-3-diethylaminopyridine, 2-(aminomethyl)-4-acetylaminopyridine, and 2-(aminomethyl)-4-trifluoromethylpyridine, respectively, all of which may be prepared by reduction of the corresponding nitrile of formula (IVC) according to the method of Sculley, et al., supra., there is obtained 1-(m-fluorophenyl)-3-[2-(6-methylpyridylmethyl)]-2-thiourea, 1-(m-fluorophenyl)-3-[2-(5-ethylpyridylethyl)]-2-thiourea, 1-(m-fluorophenyl)-3-[5-(3-amino-2-methylpyridylmethyl)]-2-thiourea, 1-(m-fluorophenyl)-3-[2-(3-chloropyridylmethyl)]-2-thiourea, 1-(m-fluorophenyl)-3-[2-(4-phenylpyridylmethyl)]-2-thiourea, 1-(m-fluorophenyl)-3-[2-(4-benzylpyridylmethyl)]-2-thiourea, 1-(m-fluorophenyl)-3-[2-(4-methoxypyridylmethyl)]-2-thiourea, 1-(m-fluorophenyl)-3-[2-(4-methylthiopyridylmethyl)]-2-thiourea, 1-(m-fluorophenyl)-3-[2-(3-nitropyridylmethyl)]-2-thiourea, 1-(m-fluorophenyl)-3-[2-(3-ethylaminopyridylmethyl)]-2-thiourea, 1-(m-fluorophenyl)-3-[2-(3-diethylaminopyridylmethyl)]-2-thiourea, 1-(m-fluorophenyl)-3-[2-(4-acetylaminopyridylmethyl)]-2-thiourea, and 1-(m-fluorophenyl)-3-[2-(4-trifluoromethylpyridylmethyl)]-2-thiourea, respectively.

EXAMPLE 6

1-(o-fluorophenyl)-3-(4-pyridylmethyl)-2-thiourea to a mixture of 5.41 grams (0.05 mole) of 4-aminomethylpyridine in 100 ml. of tetrahydrofuran there is slowly added with stirring 7.66 gms. (0.05 mole) of o-fluorophenylisothiocyanate. Upon completion of the addition, the reaction mixture is allowed to stand for 4 days at ambient temperatures and then refluxed for 30 minutes. Solvent is stripped and the residue crystallized from a mixture of ethyl acetate-ethanol-Skellysolve B (4:1:5 v/v/v) to give 6.54 gms. (50 percent of theory) of 1-(o-fluorphenyl)-3-(4-pyridylmethyl)-2-thiourea in the form of pale yellow crystals, M.P. 144.6° C.

EXAMPLE 7

1-(p-cyanophenyl)-3-(3-pyridylmethyl)-2-thiourea

To a mixture of 4.33 gms (0.04 mole) of 3-aminomethylpyridine and 100 ml. of tetrahydrofuran there is added 6.41 gms. (0.04 mole) of p-cyanophenylisothiocyanate. The reaction mixture is allowed to stand for 28 hours at ambient temperatures and then refluxed for 30 minutes. At the end of this period, the reaction mixture is diluted with sufficient dimethylformamide to give a clear solution of reflux temperature. The hot solution is diluted with water to a volume of 400 ml. and allowed to cool. The crystalline precipitate is removed by filtration, washed with water and dried to give 7.37 gms. (69 percent of theory) of 1-(p-cyanophenyl)-3-(3-pyridylmethyl)-2-thiourea in the form of colorless needles, M. P. 181.1° C.

EXAMPLE 8

1-(p-nitrophenyl)-3-(3-pyridylmethyl)-2-thiourea

Following the procedure of Example 7, supra., but replacing the p-cyanophenylisothiocyanate as used therein with an equal molar proportion of p-nitrophenylisothiocyanate there is obtained 10.01 gms. (87 percent of theory) of 1-(p-nitrophenyl)-3-(3-pyridylmethyl)-2-thiourea in the form of yellow needles, M. P. 187.9° C.

EXAMPLE 9

1-(m-nitrophenyl)-3-(3-pyridylmethyl)-2-thiourea

To a mixture of 4.33 gms. (0.04 mole) of 3-aminomethylpyridine and 100 ml. of tetrahydrofuran there is added with stirring 7.21 gms. (0.04 mole) of 3-nitrophenylisothiocyanate. The resulting mixture is allowed to stand at ambient temperatures for 28 hours and then it is refluxed for 30 minutes. The reaction mixture is then diluted with water to a volume of about 300 ml. and allowed to cool. Upon cooling, a crystalline precipitate appears which when separated, washed with water gives 7.28 gms. (63 percent of theory) of 1-(m-nitrophenyl)-3-(3-pyridylmethyl)-2-thiourea, M. P. 158.9° C.

EXAMPLE 10

1-(m-trifluoromethylphenyl)-3-(3-pyridylmethyl)-2-thiourea

Following the procedure of Example 9, supra., but lowering the proportion of 3-aminomethylpyridine as used therein to 3.25 gms. (0.03 mole) and replacing the 3-nitrophenylisothiocyanate as used therein with 5.7 gms. (0.028 mole) of m-trifluoromethylphenylisothiocyanate there is obtained 8.54 gms. (91 percent of theory) of 1-(m-trifluoromethylphenyl)-3-(3-pyridylmethyl)-2-thiourea in the form of colorless crystals, M. P. 143.7° C.

EXAMPLE 11

1,1'-p-phenylenebis[3-(3-pyridylmethyl)]-2-thiourea

Following the procedure of Example 9, supra., but replacing the 3-nitrophenylisothiocyanate as used therein with 3.85 gms. (0.02 mole) of p-phenylenediisothiocyanate there is obtained 8.12 gms. (99 percent of theory) of 1,1'-p-phenylenebis[3-(3-pyridylmethyl)]-2-thiourea in the form of white needles, M. P. 197.8° C.

EXAMPLE 12

1-(p-cyanophenyl)-3-(2-pyridylmethyl)-2-thiourea

To a mixture of 4.33 gms. (0.04 mole) of 2-aminomethylpyridine and 100 ml. of tetrahydrofuran there is added with stirring 6.41 gms. (0.04 mole) of p-cyanophenylisothiocyanate. The mixture is then allowed to stand at ambient temperatures for 24 hours after which it is refluxed for 15 minutes. Solvent is then removed under vacuum leaving a solid residue. Upon crystallization from ethanol-water (4:1, v/v) there is obtained 7.07 gms. (66 percent of theory) of 1-(p-cyanophenyl)-3-(2-pyridylmethyl)-2-thiourea in the form of white needles, M. P. 143.6° C.

EXAMPLE 13

1-(p-nitrophenyl)-3-(2-pyridylmethyl)-2-thiourea

Following the procedure of Example 12, supra., but replacing the p-cyanophenylisothiocyanate as used therein with an equal molar proportion of p-nitrophenylisothiocyanate there is obtained 7.14 gms. (62 percent of theory) of 1-(p-nitrophenyl)-3-(2-pyridylmethyl)-2-thiourea in the form of yellow needles, M. P. 165.4° C.

EXAMPLE 14

1-(m-nitrophenyl)-3-(2-pyridylmethyl)-2-thiourea

Following the procedure of Example 12, supra., but replacing the p-cyanophenylisothiocyanate as used therein with an equal molar proportion of m-nitrophenylisothiocyanate there is obtained 10.43 gms. (90 percent of theory) of 1-(m-nitrophenyl)-3-(2-pyridylmethyl)-2-thiourea in the form of yellow needles, M. P. 169.7° C.

EXAMPLE 15

1-(m-trifluoromethylphenyl)-3-(2-pyridylmethyl)-2-thiourea

Following the procedure of Example 12, supra., but reducing the proportion of 2-aminomethylpyridine as used therein to 3.25 gms. (0.03 mole) and replacing the p-cyanophenylisothiocyanate as used therein with 6.09 gms. (0.03 mole) of m-trifluoromethylphenylisothiocyanate there is obtained 3.74 gms. (40 percent of theory) of 1-(m-trifluoromethylphenyl)-3-(2-pyridylmethyl)-2-thiourea in the form of light blue needles. M. P. 132.6° C.

EXAMPLE 16

3-(p-cyanophenyl)-1-methyl-1-(2-pyridylmethyl)-2-thiourea

To a mixture of 4.89 gms. (0.04 mole) of 2-methylaminomethylpyridine and 100 ml. of tetrahydrofuran there is added with stirring 6.41 gms. (0.04 mole) of p-cyanophenylisothiocyanate. Upon the completion of addition, the mixture is allowed to stand overnight and is then refluxed for 2 hours. At the end of this period, the reaction mixture is diluted with methanol to a volume of about 500 ml. and allowed to cool to room temperature. The solid appearing in the reaction mixture is separated by filtration, washed with methanol and dried to give 5.5 gms. (51 percent of theory) of 3-(p-cyanophenyl)-1-methyl-1-(2-pyridylmethyl)-2-thiourea in the form of colorless crystals, M. P. 170.6° C.

Similarly, following the above procedure but replacing the 2-methylaminomethylpyridine as used therein with an equal molar proportion of 2-cyclohexylaminomethylpyridine, 2-phenylaminomethylpyridine, 2-benzylaminomethylpyridine, 2-(p-chlorophenyl)aminomethylpyridine, 2-(p-methoxyphenyl)aminomethylpyridine, 2-(p-trifluoromethylphenyl)aminomethylpyridine and 2-(p-trifluoromethoxyphenyl)aminomethylpyridine, respectively, [all of which may be prepared by reduction of the appropriate compound (IVB) according to the method of Tarbell et al., supra.], there is obtained 3-(p-cyanophenyl)-1-cyclohexyl-1-(2-pyridylmethyl)-2-thiourea, -thiourea, 3-(p-cyanophenyl)-1-phenyl-1-(2-pyridylmethyl)-2-thiourea, 3-(p-cyanophenyl)-1-benzyl-1-(2-pyridylmethyl)-2-thiourea, 3-(p-cyanophenyl)-1-p-chlorophenyl)-1-(2-pyridylmethyl)-2-thiourea, 3-(p-cyanophenyl)-1-(p-methoxy)-1-(2-pyridylmethyl)-2-thiourea, 3-(p-cyanophenyl)-1-(p-trifluoromethylphenyl)-1-(2-pyridylmethyl)-2-thiourea and 3-(p-cyanophenyl)-1-(p-trifluoromethoxyphenyl)-1-(2-pyridylmethyl)-2-thiourea, respectively.

EXAMPLE 17

3-(p-nitrophenyl)-1-methyl-1-(2-pyridylmethyl)-2-thiourea

Following the procedure of Example 16, supra., but replacing the p-cyanophenylisothiocyanate as used therein with an equal molar proportion of p-nitrophenylisothiocyanate there is obtained 8.29 gms. (69 percent of theory) pf 3-(p-nitrophenyl)-1-methyl-1-(2-pyridylmethyl)-2-thiourea in the form of pale yellow crystals, M.P. 188.1° C.

EXAMPLE 18

3-(m-nitrophenyl)-1-methyl-1-(2-pyridylmethyl)-2-thiourea

Following the procedure of Example 16, supra., but replacing the p-cyanophenylisothiocyanate as used therein with an equal molar proportion of m-nitrophenylisothiocyanate there is obtained 3.39 gms. (28 percent of theory) of 3-(m-nitrophenyl)-1-methyl-1-(2-pyridylmethyl)-2-thiourea in the form of yellow needles, M.P. 142.3° C.

EXAMPLE 19

1-(p-aminophenyl)-3-(4-pyridylmethyl)-2-thiourea

To a mixture of 5.76 gms. (0.02 mole) of 1-(p-nitrophenyl)-3-(4-pyridylmethyl)-2-thiourea, (Example 2, supra.), 200 ml. of ethanol and 65 ml. of hydrazine hydrate is added with stirring 0.5 grams of 5 percent palladium-on-carbon in 50 ml. of ethanol. The resulting mixture is allowed to stand overnight at room temperature and then refluxed for 2 to 3 hours. The hot reaction mixture is then filtered and the filtrate evaporated to remove solvents. The residue is 1-(p-aminophenyl)-3-(4-pyridylmethyl)-2-thiourea.

EXAMPLE 20

1-(p-acetamidophenyl)-3-(4-pyridylmethyl)-2-thiourea

To a chilled (circa 0° C.) solution of 5.16 gms. (0.02 mole) of 1-(p-aminophenyl)-3-(4-pyridylmethyl)-2-thiourea (Example 19, supra.) and 75 ml. of pyridine there is added dropwise 1.48 gms. (0.02 mole) of acetyl chloride with stirring, while maintaining the temperature at circa 0° C. Upon completion of the addition, the reaction mixture is stirred for an additional 30 minutes and then allowed to stand at room temperature for about 16 hours. Solvent is then removed in vacuo and the residue suspended in water. Water is then removed to give a residue of 1-(p-acetomidophenyl)-3-(4-pyridylmethyl)-2-thiourea.

EXAMPLE 21

1-(p-ethylaminophenyl)-3-(4-pyridylmethyl)-2-thiourea

To 3.54 gms. (0.01 mole) of 1-(p-trifluoroacetamidophenyl)-3-(4-pyridylmethyl)-2-thiourea [prepared by reacting 1-(p-aminophenyl)-3-(4-pyridylmethyl)-2-thiourea (Example 19, supra.) with trifluoroacetic anhydride (method of Hickinbottom, Reactions of Organic Compounds, Longmans, London, 1963)] there is added 6.24 gms. (0.04 mole) of ethyl iodide in 50 ml. of dry acetone. Acetone is stripped and the residue added to 50 ml. of water. The aqueous mixture is warmed to reflux for about 30 minutes and then allowed to stand overnight. The mixture is then stripped of water to give 1-(p-ethylaminophenyl)-3-(4-pyridylmethyl)-2-thiourea.

EXAMPLE 22

1-(4-pyridylmethyl)-3-(3-trifluoromethylphenyl)-2-thiourea-N-oxide

To 15.55 gms. (0.005 mole) of 1-(4-pyridylmethyl)-3-(3-trifluoromethylphenyl)-2-thiourea (Example 3) in 100 ml. of glacial acetic acid there is added 8 ml. of 30 percent hydrogen peroxide at room temperature. The reaction mixture is set aside for overnight and then warmed circa 60°–80° C. for 4 hours. The solvent is then evaporated in vacuo. The residue is treated with water and then evaporated in vacuo again. The residue is then suspended in 100 ml. of water and adjusted to a pH of 7 with sodium bicarbonate. The solid which precipitates is separated, washed with water and dried. Crystallization from ethanol gives 1-(4-pyridylmethyl)-3-(3-trifluoromethylphenyl)-2-thiourea-N-oxide as yellow crystals.

Similarly, following the above procedure but replacing the 1-(4-pyridylmethyl)-3-(3-trifluoromethylphenyl)-2-thiourea as used therein with any other compound of the formula (I) such as therein prepared in Examples 1–21, supra., the corresponding N-oxide of formula (IX) is obtained.

EXAMPLE 23

To 3.0 gms. of 3-(m-nitrophenyl)-1-methyl-1-(2-pyridylmethyl)-2-thiourea (Example 18, supra.) there is added sufficient ethanol to form a solution. Hydrogen chloride is bubbled into the solution until a solid precipitates. The solid is separated, washed with cold ethanol and dried to give 3-(m-nitrophenyl)-1-methyl-1-(2-pyridylmethyl)-2-thiourea hydrochloride.

Similarly, following the above procedure but replacing the 3-(m-nitrophenyl)-1-methyl-1-(2-pyridylmethyl)-2-thiourea as used therein with any other compound of the formula (I) or pyridyl N-oxide thereof such as those prepared in Examples 1–22, supra., the corresponding hydrochloride salt is obtained.

The following examples illustrate the compositions and uses of the compounds of the invention and the method of the invention.

EXAMPLE 24

Tablets

One thousand tablets for oral use, each containing 250 mg. of 1-(4-pyridylmethyl)-3-(3-trifluoromethylphenyl)-2-thiourea as the essential active ingredient are prepared from the following ingredients:

| | |
|---|---|
| essential active ingredient | 250 gms. |
| lactose | 200 gms. |
| microcrystalline cellulose N.F. | 50 gms. |
| starch | 5 gms. |
| magnesium stearate powder | 1 gm. |

The ingredients are thoroughly mixed and slugged. The slugs are broken down by forcing through a screen and the resulting granules are then compressed into tablets.

These tablets are useful in controlling atonic uterine hemorrhage in adult humans when given at a dose of 1 to 3 tablets. High blood levels of $PGF_2\alpha$ and $PGE_2$ are observed for from 6 to 8 hours after administration.

The tablets are also useful for treating male mammals for infertility when 1 to 3 tablets are given 3 to 4 times a week.

EXAMPLE 25

Capsules

One thousand two-piece hard gelatin capsules for oral use, each capsule containing 250 mg. of 1-(p-fluorophenyl)-3-(4-pyridylmethyl)-2-thiourea as the essential active ingredient are prepared from the following ingredients:

| | |
|---|---|
| essential active ingredient | 250 gms. |
| lactose | 200 gms. |
| talc | 25 gms. |
| magnesium stearate | 2 gms. |

The finely powdered materials are mixed thoroughly, then filled into hard gelatin capsules of appropriate size. The capsules are given to adult humans suffering from burns at a dose of 1 to 3 capsules given 3 to 14 times a week, resulting in an acceleration of healing and epidermal proliferation.

EXAMPLE 26

Aqueous Solution

An aqueous oral preparation containing in each teaspoonful (5 ml.) 500 mg. of essential active ingredient is prepared from the following:

| | | |
|---|---|---|
| 1-(4-pyridylmethyl-3-(3-trifluoromethylphenyl)-2-thiourea | 500 | gms. |
| glycerin | 2000 | ml. |
| tragacanth powder | 50 | gms. |
| propyl paraben | 3 | gms. |
| sucrose | 6.5 | gms. |
| orange oil flavor | 5 | gms. |
| deionized water, q.s. | 5000 | ml. |

The above oral preparation may be given to adult humans at a dose of 1 to 3 teaspoonfuls 3 to 14 times weekly to accelerate the healing of epidermal wounds.

EXAMPLE 27

Injectable

A sterile suspension suitable for intramuscular injection and containing in each milliliter 250 mg. of 1-(4-pyridylmethyl)-3-(3-trifluoromethylphenyl)-2-thiourea is prepared from the following ingredients:

| | | |
|---|---|---|
| 1-(4-pyridylmethyl)-3-(3-tri- | | |
| fluoromethylphenyl)-2-thiourea | 250 | gms. |
| benzyl benzoate | 200 | ml. |
| methylparaben | 1.5 | gms. |
| propylparaben | 0.5 | gms. |
| cottonseed oil q.s. | 1000 | ml. |

The above sterile injectable is useful in controlling the development of thrombi following saphenectomy when given at a dose of 1 to 4 ml. administered 2 to 6 hours prior to said saphenectomy.

EXAMPLE 28

Suppository

One thousand suppositories, each weighing 4.0 gms. and containing 500 mg. of 1-(p-fluorophenyl)-3-(4-pyridylmethyl)-2-thiourea as the essential active ingredient are prepared from the following ingredients:

| | |
|---|---|
| essential active ingredient | 500 gms. |
| propylene glycol | 2000 gms. |
| polyethylene glycol 4000 | 1000 gms. |
| polyethylene glycol 400 | 500 gms. |

The essential active ingredient is added to the propylene glycol and the mixture milled until uniformly dispersed. The polyethylene glycol 4000 is melted and the propylene glycol dispersion added. The suspension is poured into molds and allowed to cool and solidify.

These suppositories are useful for controlling development of thrombi in mammals when given rectally at a dose of 1 suppository 3 to 7 times a week.

EXAMPLE 29

Various compounds of the formula (I) are admixed with water and administered orally to groups of 5 male Carworth rats (weighing 250–275 gms. each) at a dosage of 100 mg. per kilogram of body weight. The rats are prepared by fasting overnight (16 hours) prior to administration. About 3 hours after administration, tails are clipped and the rats bled. 5 ml. of blood is collected in citrated syringes (0.1 ml. of 3.8 percent w/v sodium citrate per ml. of whole blood). The collected blood is centrifuged at 900 RPM for 15 minutes and the platelet rich plasma separated and pooled for each group of 5 rats. For each 1.0 mls. of pooled plasma there is added 0.5 ml. of 0.15 M sodium phosphate buffer (pH 7.4). The resulting mixture is allowed to stand at room temperature for 30 minutes and then 0.5 mls. of sodium fluoride (4 mgs./ml. aqueous solution) is added. The mixture is then incubated at 37° C. for 60 minutes, cooled under running tap water and centrifuged at 2500 RPM for 20 minutes. The supernatant solution is separated and analyzed for $PGF_2\alpha$ concentration by the method of Kirton et al.; Biochemical and Biophysical Res. Comm., Vol. 47, 903 (1972).

The compounds employed and the results obtained are given in Table I below. Group A does not represent the invention but is a control group of 5 rats which did not receive an administration of a compound (I).

TABLE I

| Group | Compound (1) Administered | Concentration of $PGF_2\alpha$ Found (ng./ml.) |
|---|---|---|
| A (Control) | None | 33.8 ± 4.2 |
| B | 1-(4-pyridylmethyl)-3-(3-trifluoromethylphenyl)-2-thiourea | 139.6 ± 20.0 |

TABLE I-continued

| Group | Compound (1) Administered | Concentration of $PGF_2\alpha$ Found (ng./ml.) |
|---|---|---|
| C | 1-(p-fluorophenyl)-3-(4-pyridylmethyl)-2-thiourea | 110.6 ± 12.9 |

Similarly, repeating the above procedure but replacing the compounds of formula (I) as used therein with any other compounds of the formula (I), or of the formula (IX) and the pharmaceutically acceptable acid addition salts thereof prepared according to Examples 1–23, supra., similar observations of increased prostaglandin production are made.

A further group of compounds of the invention are those compounds of Formula I wherein $R_1$, $R_6$ and $R_7$ are hydrogen; $R_2$ is selected from the group consisting of hydrogen, halogen, alkyl of one to four carbon atoms, inclusive, alkoxy of one to four carbon atoms, inclusive, and trifluoromethyl; $R_3$ and $R_4$ are the same or different and are hydrogen or alkyl of one to four carbon atoms, inclusive; $R_5$ is selected from the group consisting of hydrogen, halogen, nitro, trifluoromethyl, cyano, alkyl of one to four carbon atoms, inclusive, and alkoxy of one to four carbon atoms, inclusive; $n$ is one or two; provided that when $R_2$, $R_4$ and $R_5$ are each hydrogen, then $R_3$ is alkyl of one to four carbon atoms, inclusive, and further provided that when $R_5$ is halogen or alkoxy, then $R_3$ is alkyl of one to four carbon atoms, inclusive.

The N-oxides of these compounds are also a portion of the invention. These groupings of compounds are used in the same manner as the larger generic groups and formulated into like pharmaceutical compositions.

We claim:

1. A method for increasing the production of endogenous prostaglandins by a mammal which comprises administering to said mammal an effective amount of a compound of the formula:

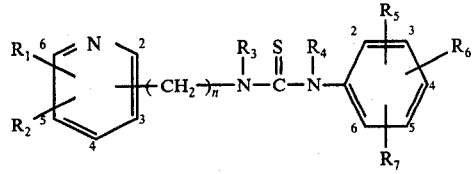

a pyridyl N-oxide thereof and a pharmaceutically acceptable acid addtion salt thereof wherein $R_1$ and $R_2$ are each hydrogen, halogen, alkyl of one to six carbon atoms, inclusive, alkenyl of two to six carbon atoms, inclusive, cycloalkyl of three to six carbon atoms, inclusive, phenyl, alkoxy of one to 12 carbon atoms, inclusive, alkylthio of one to 12 carbon atoms, inclusive, nitro, amino, alkylamino with alkyl of one to 12 carbon atoms, inclusive, dialkylamino with each alkyl of one to 12 carbon atoms, inclusive, alkanoylamine with alkyl of one to 12 carbon atoms, inclusive, or trihalomethyl;

$R_3$ and $R_4$ are each hydrogen, alkyl of one to four carbon atoms, inclusive, cycloalkyl of three to eight carbon atoms, inclusive, aryl of six to 12 carbon atoms, inclusive, aralkyl of seven to 12 carbon atoms, inclusive, and aryl of six to 12 carbon atoms, inclusive, said aryl substituted with halogen, alkoxy of one to four carbon atoms, inclusive, halogen substituted alkyl of one to four carbon atoms, inclusive, and halogen substituted alkoxy of one to four carbon atoms, inclusive; $R_5$ is hydrogen, halogen, alkyl of one to 12 carbon atoms, inclusive, alkenyl of two to 12 carbon atoms, inclusive, cycloalkyl of three to eight carbon atoms, inclusive, aryl of six to 12 carbon atoms, inclusive, aralkyl of seven to 12 carbon atoms, inclusive, alkoxy of one to 12 carbon atoms, inclusive, and halogen substituted alkyl of one to 12 carbon atoms, inclusive, halogen substituted alkenyl of two to 12 carbon atoms, inclusive, halogen substituted cycloalkyl of three to eight carbon atoms, inclusive, halogen substituted aryl of six to 12 carbon atoms, inclusive, and halogen substituted aralkyl of seven to 12 carbon atoms, inclusive; $R_6$ and $R_7$ are each nitro, amino, alkanoylamino with alkyl of one to 12 carbon atoms, inclusive, alkylamino with alkyl of one to 12 carbon atoms, inclusive, dialkylamino with each alkyl of one to 12 carbon atoms, inclusive, alkylthio with alkyl of one to 12 carbon atoms, inclusive, arylthio of six to 12 carbon atoms, inclusive, aryloxy of six to 12 carbon atoms, inclusive, and a group $R_5$ as previously defined; and $n$ is an integer of from one to two, inclusive.

2. A method according to claim 1 wherein there is an increase in the production of $9\alpha,11\alpha$, 5-trihydroxy prosta-5,13-dioenoic acid by the mammalian blood platelets.

3. A method according to claim 1 wherein said prostaglandins are selected from $11\alpha$, 15-dihydroxy-9-keto-prosta-5,13-dienoic acid and $9\alpha, 11\alpha,15$-trihydroxyprosta-5,13-dienoic acid.

4. A method according to claim 1 wherein said effective amount is within the range of from about 0.1 to about 500 mg. per kilogram body weight of said mammal.

5. A method according to claim 1 wherein said mammal is a human.

6. A method according to claim 1 wherein said mammal is suffering from atonic uterine bleeding whereby uterine tone is restored.

7. A method according to claim 6 wherein said mammal is a human.

8. A method according to claim 6 wherein said compound is administered within from 1 to 6 hours prior to said mammal undergoing abortion or delivery of a fetus.

9. A method according to claim 6 wherein said effective amount is within the range of from about 0.1 to about 500 mg. per kilogram of body weight of the recipient mammal.

10. A method according to claim 1 wherein said mammal is suffering from an epidermal injury whereby healing is accelerated.

11. A method according to claim 10 wherein said mammal is a human.

12. A method according to claim 10 wherein said effective amount is within the range of from about 0.1 to 500 mg. per kilogram of body weight of the recipient.

13. A method according to claim 10 wherein said compound is administered within from about 1 to 6 hours prior to the epidermal injury.

14. A method according to claim 1 wherein said mammal is a male suffering from infertility, whereby fertility is improved.

15. A method according to claim 14 wherein said mammal is a human.

16. A method according to claim 15 wherein said effective amount is within the range of from about 0.1 to about 500 mg. per kilogram body weight of said mammal.

17. A method according to claim 1 wherein said mammal is suffering from a condition susceptible to developing thrombi, whereby the development of said thrombi is controlled or prevented.

18. A method according to claim 17 wherein said mammal is a human.

19. A method according to claim 17 wherein said effective amount is within the range of from about 0.1 to about 500 mg. per kilogram body weight of the recipient mammal.

20. A method of increasing the production of endogenous prostaglandins by a mammal which comprises administering to said mammal an effective amount of a compound selected from those of formula:

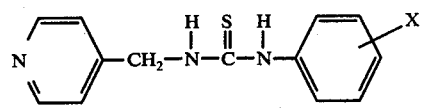

pyridyl N-oxides thereof and the pharmaceutically acceptable acid addition salts thereof wherein X is selected from hydrogeon, halogen, nitro, and trihalomethyl.

21. A method according to claim 20 wherein said prostaglandins are selected from $11\alpha,15$-dihydroxy-9-keto-prosta5,13-dienoic acid and $9\alpha, 11\alpha,15$-trihydroxyprosta-5,13-dienoic acid.

22. A method according to claim 20 wherein said effective amount is within the range of from about 0.1 to about 500 mg. per kilogram body weight of said mammal.

23. A method according to claim 20 wherein said mammal is a human.

24. A method according to claim 20 wherein said compound is 1-(4-pyridylmethyl)-3-(2-trifluoromethylphenyl)thiourea.

25. A method according to claim 20 wherein said compound is 1-(4-pyridylmethyl)-3-(3-trifluoromethylphenyl)thiourea.

* * * * *